United States Patent
Luo

(10) Patent No.: US 11,355,713 B2
(45) Date of Patent: Jun. 7, 2022

(54) HOLE TRANSPORT MATERIAL, MANUFACTURING METHOD THEREOF, AND ELECTROLUMINESCENT DEVICE THEREOF

(71) Applicant: WUHAN CHINA STAR OPTOELECTRONICS SEMICONDUCTOR DISPLAY TECHNOLOGY CO., LTD., Hubei (CN)

(72) Inventor: Jiajia Luo, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 366 days.

(21) Appl. No.: 16/629,970

(22) PCT Filed: Nov. 12, 2019

(86) PCT No.: PCT/CN2019/117379
§ 371 (c)(1),
(2) Date: Feb. 10, 2020

(87) PCT Pub. No.: WO2020/258651
PCT Pub. Date: Dec. 30, 2020

(65) Prior Publication Data
US 2020/0403162 A1    Dec. 24, 2020

(51) Int. Cl.
*H01L 51/50* (2006.01)
*H01L 51/00* (2006.01)
(Continued)

(52) U.S. Cl.
CPC ........ *H01L 51/0072* (2013.01); *C07D 241/48* (2013.01); *C07D 401/14* (2013.01);
(Continued)

(58) Field of Classification Search
CPC ............. H01L 51/0072; H01L 51/0025; H01L 51/0061; H01L 51/5056; H01L 51/5012; H01L 51/504; H01L 51/50
See application file for complete search history.

(56) References Cited

U.S. PATENT DOCUMENTS

2005/0014018 A1*  1/2005  Klubek ............... H01L 51/0059
                                                                         428/917
2012/0164070 A1   6/2012  Black et al.
(Continued)

FOREIGN PATENT DOCUMENTS

CN        101951904 A    1/2011
CN        104136430 A    11/2014
(Continued)

*Primary Examiner* — Omar F Mojaddedi
(74) *Attorney, Agent, or Firm* — The Roy Gross Law Firm, LLC; Roy Gross

(57) ABSTRACT

The present invention provides an improved hole transport material, manufacturing method and an electroluminescent device having a central core made of tetramethyldihydrophenazine. A structural formula of the hole transport material is:

(Continued)

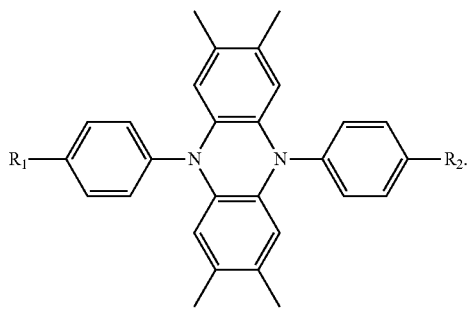

The present invention adjusts the structure of donor units to change a capability of providing electrons thereof, designs a hole transport material of a high mobility and reasonable wires, and the material improves the compounding efficiency.

1 Claim, 1 Drawing Sheet

(51) Int. Cl.
*H01L 51/52* (2006.01)
*C07D 241/48* (2006.01)
*C09K 11/06* (2006.01)
*C07D 403/14* (2006.01)
*C07D 401/14* (2006.01)

(52) U.S. Cl.
CPC ............ *C07D 403/14* (2013.01); *C09K 11/06* (2013.01); *H01L 51/0025* (2013.01); *H01L 51/0061* (2013.01); *C09K 2211/1018* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5265* (2013.01); *H01L 2251/552* (2013.01)

(56) References Cited

U.S. PATENT DOCUMENTS

2017/0374721 A1* 12/2017 Neyts .................. H01L 51/5268
2018/0090683 A1* 3/2018 Béalle ................. H01L 51/0094
2019/0081263 A1* 3/2019 Park .................... H01L 51/5056

FOREIGN PATENT DOCUMENTS

| CN | 104638146 A | 5/2015 |
| CN | 108948041 A | 12/2018 |
| CN | 109851616 A | 6/2019 |
| CN | 110299460 A | 10/2019 |
| TW | 201509920 A | 3/2015 |

* cited by examiner

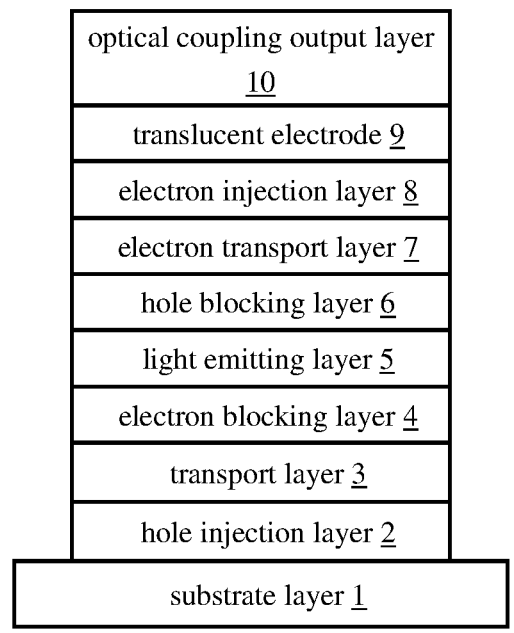

HOLE TRANSPORT MATERIAL, MANUFACTURING METHOD THEREOF, AND ELECTROLUMINESCENT DEVICE THEREOF

FIELD OF INVENTION

The present invention relates to a field of photoelectric technologies, especially to a hole transport material, a manufacturing method thereof, and an electroluminescent device thereof.

BACKGROUND OF INVENTION

Organic light emitting diodes (OLEDs) have advantages of active luminescence without backlights, high luminous efficiency, wide view angles, short response times, large temperature adaption range, comparative simple manufacturing processes, low drive voltages, low energy consumption, light weight and compactness, and flexible display and huge application prospects, and therefore attract many researchers' attention.

SUMMARY OF INVENTION

Technical Issue

In an organic light emitting diode (OLED), a luminous objective material playing a leading role is of paramount importance. A Luminous objective material used by early OLEDs is a fluorescent material. Because in an OLED, a proportion of excitons of singlet to excitons of triplet is 1:3, an OLED based on the fluorescent material has a theoretical internal quantum efficiency (IQE) that can only reach 25%, which extremely restricts applications of fluorescent electroluminescent devices. A heavy metal complex phosphorescent material, because of spin-orbit coupling, can simultaneously use the excitons of singlet and triplet to achieve IQE of 100%. However, the used heavy metal is generally precious metal such as Ir, Pt. Furthermore, the metal complex phosphorescent material, still needs breakthrough in the aspect of blue materials.

In the current top emission OLED devices, a hole transport material is the thickest layer, and an energy level and a hole mobility thereof are contradictory. developing a hole transport material with a matching energy level and a high mobility is urgent.

Technical Solution

The present invention aims at the above issue, by clever molecule design, on the basis of a structure of tetramethyldihydrophenazine, compounds a series of hole transport materials with suitable HOMO/LUMO energy levels, identifies structures of the materials by spectrometric analysis, and calculates out performance thereof in a TOP device.

The present invention provides a hole transport material, comprising a central core made of tetramethyldihydrophenazine, wherein a structural formula of the hole transport material is:

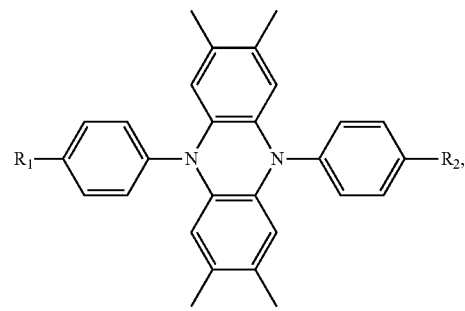

wherein each of the $R_1$ group and the $R_2$ group is selected from structural formulas as follows:

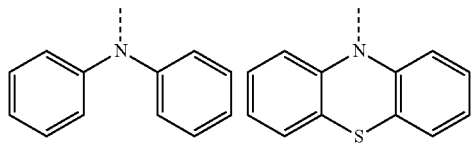

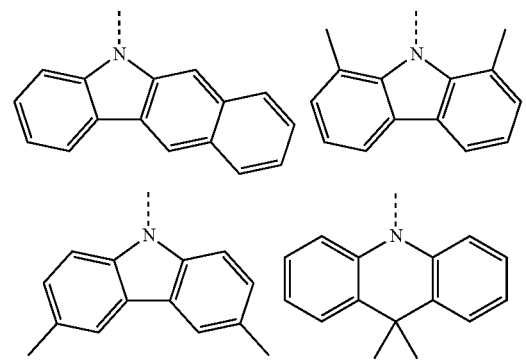

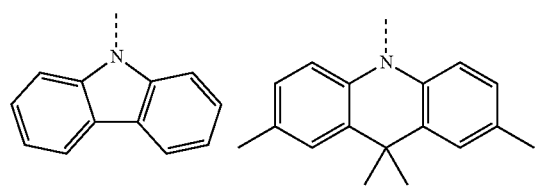

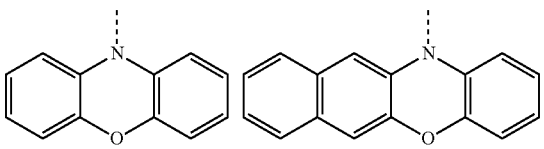

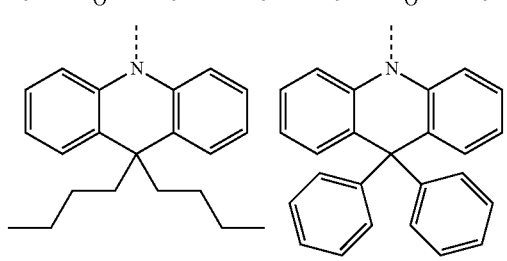

-continued

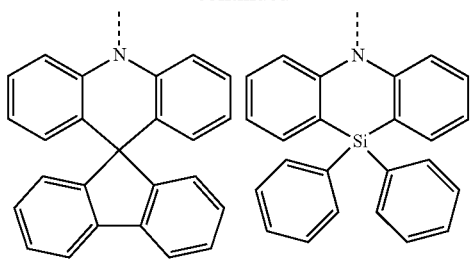

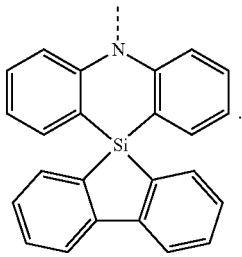

The hole transport material is selected from structural formulas as follows:

Compound 1

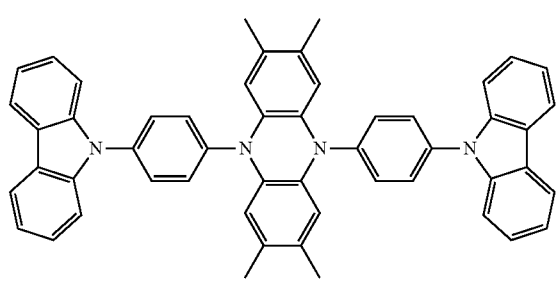

Compound 2

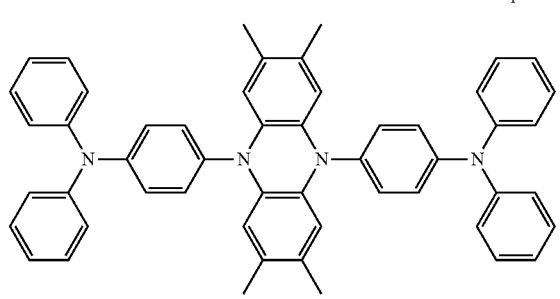

Compound 3

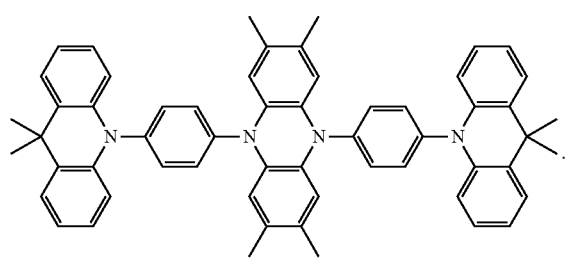

The hole transport material is composed of tetramethyl-dihydrophenazine including an electron donor and an electron donor in a periphery, and a structural formula of the central core is as follows:

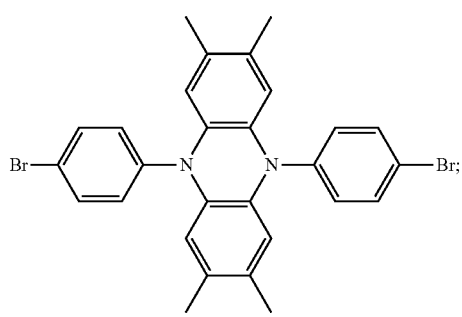 [SMILES: Cc1cc2c(cc1C)N(c1ccc(Br)cc1)c1cc(C)c(C)cc1N2c1ccc(Br)cc1]

the electron donor is selected from

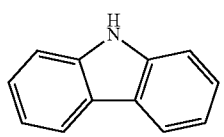 [SMILES: c1ccc2c(c1)[nH]c1ccccc12]

(carbazole),

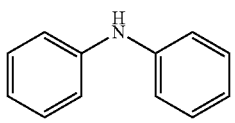 [SMILES: c1ccc(Nc2ccccc2)cc1]

(diphenylamine), and

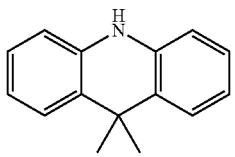 [SMILES: CC1(C)c2ccccc2Nc2ccccc21]

(9,9'-dimethylacridine).

The electroluminescent device of the present invention comprises a substrate layer, a hole injection layer, a transport layer, an electron blocking layer, light emitting layer, hole blocking layer, an electron transport layer, electron injection layer, translucent electrode, and an optical coupling output layer that are sequentially stacked on one another;

wherein the substrate layer 1 comprises glass and a total reflection underlay layer including an indium tin oxide (ITO) layer, an Ag layer and an ITO layer that are stacked sequentially, and the Ag layer is a reflective surface configured to make an output light emitted from a top of the device;

wherein the hole injection layer 2 is configured to inject holes from the ITO layers into an organic light emitting diode (OLED) device, and is made of $MoO_3$;

wherein the hole transport layer 3 is configured to transport the holes injected and is capable of adjusting a resonant wavelength of a microcavity by adjusting a thickness of the hole transport layer, and the hole transport layer is made of the hole transport material;

wherein the electron blocking layer 4 is configured to block and hold electrons injected into the light emitting layer in the light emitting layer to prevent the electrons from being transported to the hole transport layer, and to restrict a composite region of excitons in the light emitting layer, and the electron blocking layer is made of (4-[1-[4-[bis(4-methylphenyl)amino]phenyl]cyclohexyl]-N-(3-methylphenyl)-N-(4-methylphenyl)aniline (TAPC);

wherein the light emitting layer 5 is configured to combine the holes and the electrons to form excitons, a fluorescent material emits light by the excitons, and the light emitting layer is made of 4,4'-bis(9-carbazole)biphenyl: tris(2-phenylpyridine)iridium (III) doped;

wherein the hole blocking layer 6 is configured to block and hold holes injected into the light emitting layer in light emitting layer to prevent the holes from being transported to the electron transport layer, and to restrict, and to restrict a composite region of excitons in the light emitting layer, and the hole blocking layer is made of 1,3,5-Tris(3-pyridyl-3-phenyl)benzene (Tm3PyPB);

wherein the electron transport layer 7 is configured to transport the electrons injected, is made of 1,3,5-Tris(3-pyridyl-3-phenyl)benzene Tm3PyPB and 8-Hydroxyquinoline aluminum salt (LiQ), and the electron transport layer is configured to transport the electrons to the light emitting layer;

wherein the electron injection layer 8 injects electrons into the OLED device;

wherein the translucent cathode layer 9 is configured to translucent emission and transmission, is capable of adjusting strength of the microcavity, and is made of magnesium/silver translucent electrode; and wherein the coupling output layer 10 is configured to implement coupling extraction to light and enhance light output rate, and the coupling output layer is made of 4,4',4''-tris[4-(carbazol-9-yl)phenyl]amine (TCTA).

The present invention also provides for manufacturing a hole transport material, comprising:

step 1) proportionally adding raw materials including a central core raw material and an electron donor, and mixing the raw materials with a solvent as a reaction solution;

step 2) adding a catalyst of palladium (II) acetate (Pd(OAc)$_2$) and a tri-tert-butylphosphine tetrafluoroborate into the reaction solution, and adding toluene free of water and oxygen under an atmosphere of argon gas in the reaction solution, heating the raw materials, the solvent, the catalyst, and the toluene in the reaction solution for reaction by 20-24 hours, and cooling the reaction solution to a room temperature;

step 3) pouring the reaction solution into ice water, extracting extracts of organic phase three times by dichloromethane to combine the extract of organic phase, and spinning the extracts of organic phase combined to form silicone; and step 4) implementing separation and purification of column chromatography to acquire white powder to acquire a finished product of the hole transport material.

The hole transport material is composed of tetramethyldihydrophenazine including an electron donor and an electron donor in a periphery, and a structural formula of the central core is as follows:

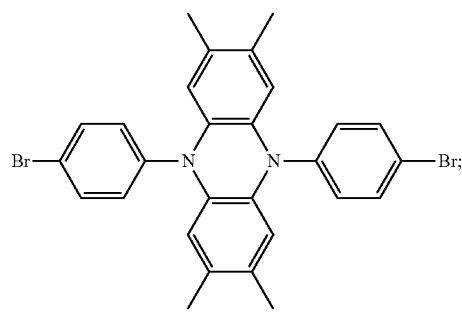 [SMILES: Cc1cc2c(cc1C)N(c1ccc(Br)cc1)c1cc(C)c(C)cc1N2c1ccc(Br)cc1]

the electron donor is selected from

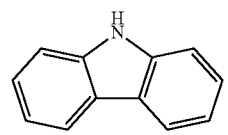

(carbazole),

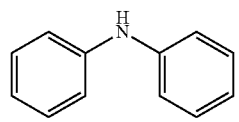 [SMILES: c1ccc(Nc2ccccc2)cc1]

(diphenylamine), and

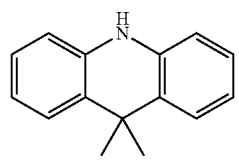 [SMILES: CC1(C)c2ccccc2Nc2ccccc21]

(9,9'-dimethylacridine).

An input amount of the central core is 2.73 g, and a molar amount of the central core is 5 mmol. An input amount of the electron donor is 2.0-2.5 g, a molar amount of the electron donor is 12 mmol, an input amount of the palladium (II) acetate is 0.18 g, an molar amount of the palladium (II) acetate is 0.8 mmol, an input amount of the tri-tert-butylphosphine tetrafluoroborate is 0.68 g, and a molar amount of the tri-tert-butylphosphine tetrafluoroborate is 2.4 mmol.

Advantages

Compared to the prior art, the present invention provides an improved hole transport material, adjusts structures of the donor unit by combination of different functional groups under the basis of the central core made of tetramethyldihydrophenazine to change the capability of providing electrons thereof. Such design, comparing to a mobility of a conventional HTL material, has the hole transport material with a higher mobility. Because of the higher mobility, holes transported to the light emitting layer are increased, the compounding rate of holes and electrons are raised such that the light emitting efficiency of the device is increased. Specific performance is increasing current efficiency of the device to achieve compounding of the organic light emitting material and application in the light emitting device.

DESCRIPTION OF DRAWINGS

FIG. 1 is a schematic structural view of an electroluminescent device of the present invention.

DETAILED DESCRIPTION OF PREFERRED EMBODIMENTS

In a field of organic light emitting diode (OLED) display screens, a hole transport material is configured to transport holes and simultaneously perform a function of adjusting a microcavity, a consumption amount thereof is the greatest in the entire OLED device, and a thickness of the film layers is also the greatest. A mobility of holes thereof is the key factor of efficiency and lifespan of the OLED device. The present invention on the basis of the central core of the tetramethyldihydrophenazine designs and compounds a series of hole transport materials for compounds. Finally, electroluminescent devices based on the targeted hole transport material have very high efficiency. An objective of the present invention is to achieve matching Highest Occupied Molecular Orbital (HOMO)/Lowest Unoccupied Molecular Orbital (LUMO) energy level, compounding of a hole transport material with high mobility and applications thereof in light emitting devices.

To achieve the above inventive objective of the, the present invention provides a hole transport material comprising a central core made of tetramethyldihydrophenazine. A structural formula of the hole transport material is:

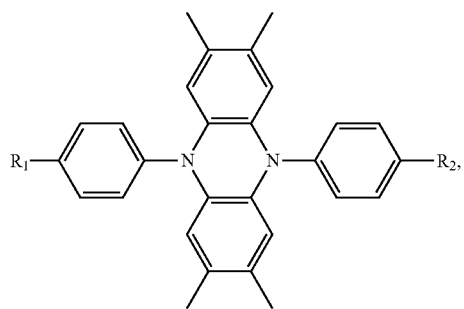

wherein each of the $R_1$ and the $R_2$ groups can be selected from structural formulas as follows:

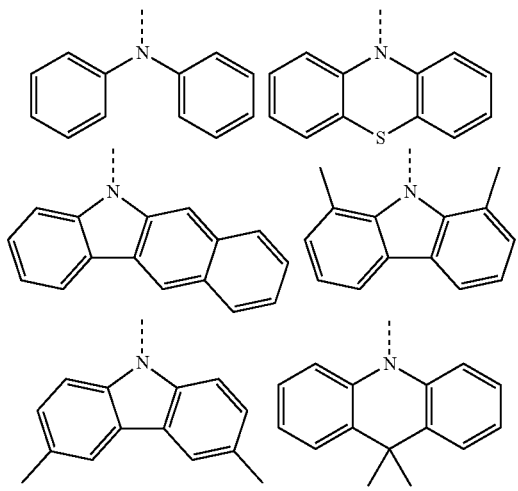

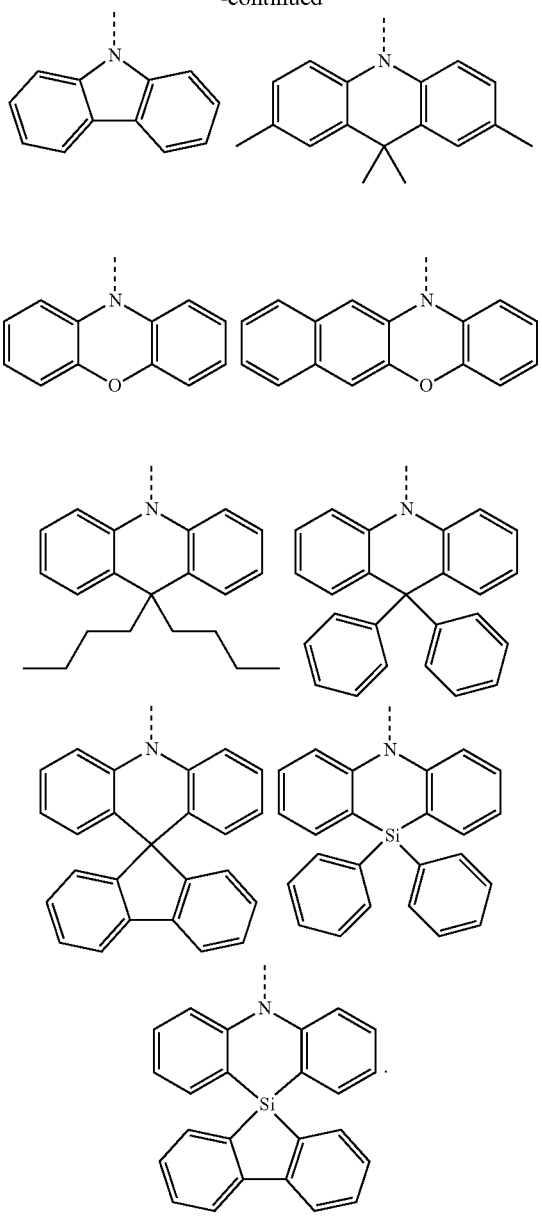

By the structural formula of the hole transport material acquired by mutual reaction of the raw material of the central core and electron donors, the hole transport material is selected from three compounds as follows:

Compound 1

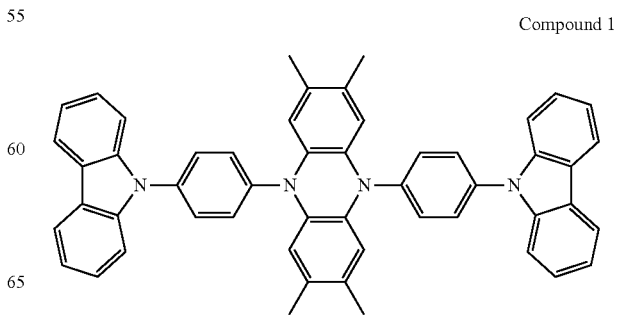

-continued

Compound 2

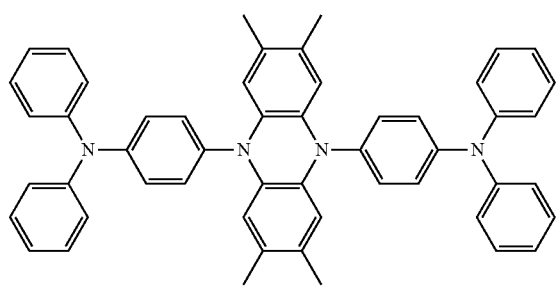

Compound 3

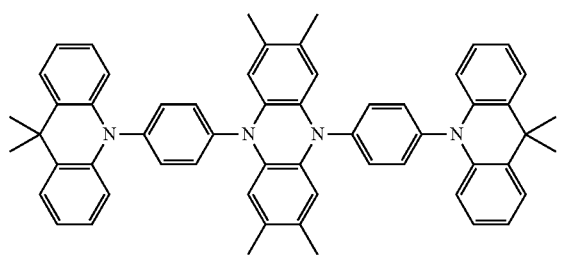

The present invention also provides a method for manufacturing a hole transport material comprising: step 1), step 2), step 3), and step 4).

The step 1) proportionally adds raw materials including a central core raw material and an electron donor, and mixing the raw materials with a solvent as a reaction solution.

The step 2) adds a catalyst of palladium (II) acetate (Pd(OAc)$_2$) and a tri-tert-butylphosphine tetrafluoroborate into the reaction solution, and adding toluene free of water and oxygen under an atmosphere of argon gas in the reaction solution, heating the raw materials, the solvent, the catalyst, and the toluene in the reaction solution for reaction by 20-24 hours, and cooling the reaction solution to a room temperature.

The step 3) pours the reaction solution into ice water, extracting extracts of organic phase three times by dichloromethane to combine the extract of organic phase, and spinning the extracts of organic phase combined to form silicone.

The step 4) implements separation and purification of column chromatography to acquire white powder to acquire a finished product of the hole transport material.

The solvent is made of palladium (II) acetate (Pd(OAc)$_2$) and tri-tert-butylphosphine tetrafluoroborate ((t-Bu)$_3$HPBF$_4$).

Preferably, the step 2) adds toluene free of water and oxygen under an atmosphere of argon gas in the reaction solution, for reaction at 120° C. by 24 hours, and cools the reaction solution to a room temperature.

Preferably, an input amount of the electron donor is 2.73 g, and a molar amount of the electron donor is 5 mmol. An input amount of the electron donor is 2.0-2.5 g, a molar amount of the electron donor is 12 mmol, an input amount of the palladium (II) acetate is 0.18 g, an molar amount of the palladium (II) acetate is 0.8 mmol, an input amount of the tri-tert-butylphosphine tetrafluoroborate is 0.68 g, and a molar amount of the tri-tert-butylphosphine tetrafluoroborate is 2.4 mmol.

Preferably, the step 4) adds dichloromethane and hexane for implementing separation and purification of column chromatography, a volume ratio of dichloromethane and hexane is 1:5. After separation and purification of column chromatography, white powder is acquired, i.e., the hole transport material.

Three embodiments as follows are introduced for explaining compounding methods and compounding reactions of hole transport materials of three structural formulas.

First Embodiment

A hole transport material 1 is compounded, a compounding path thereof is as follows:

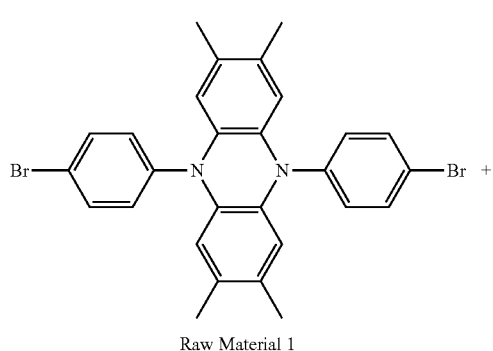

Raw Material 1

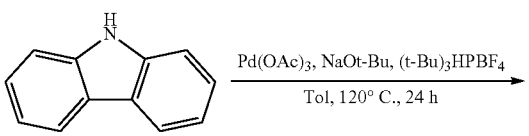

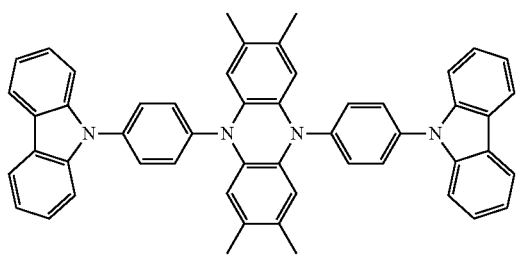

Compound 1

Compounding Step:

A raw material 1

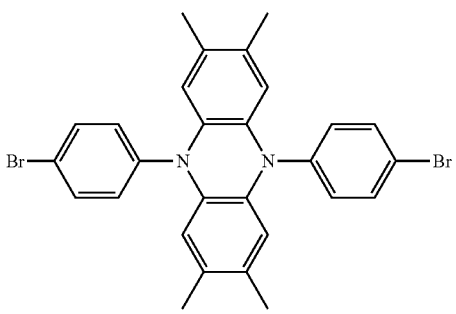

(2.73 g, 5 mmol), carbazole

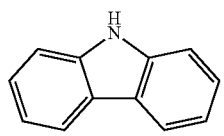 [SMILES: c1ccc2c(c1)[nH]c1ccccc12]

(2.00 g, 12 mmol), palladium (II) acetate (0.18 g, 0.8 mmol) and tri-tert-butylphosphine tetrafluoroborate (0.68 g, 2.4 mmol) are added into a dual mouth bottle of 250 mL, and then NaOt-Bu (1.16 g, 12 mmol) is added into a glovebox, toluene of 100 mL free of water and oxygen is added into the reaction solution in advance under an atmosphere of argon gas for reaction at 120° C. by 24 hours. The reaction solution above are cooled to a room temperature, and the reaction solution is poured into ice water of 200 mL, extracts of organic phase are extracted three times by dichloromethane to combine the extract of organic phase, and the extracts of organic phase combined are spun to form silicone. Separation and purification of column chromatography (dichloromethane:hexane, v:v, 1:5) is implemented to acquire white powder of 3.3 g, and a yield rate is 92%. After spectrometric analysis, MS (EI) m/z: [M]+ is 720.31.

Second Embodiment

A hole transport material 2 is compounded, a compounding path thereof is as follows:

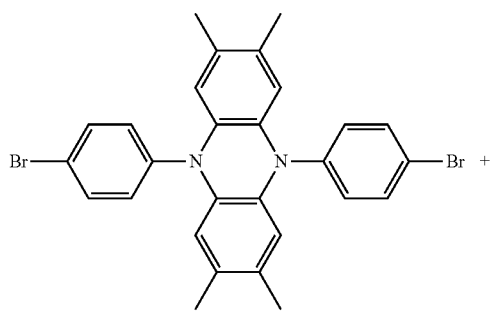
Raw Material 1

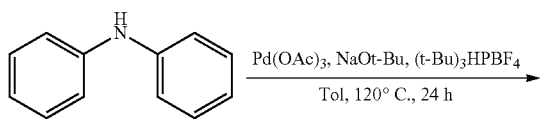

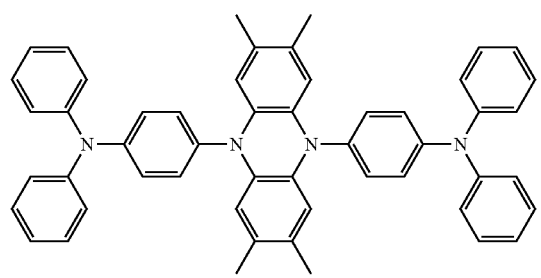
Compound 2

A compounding step:
A raw material 1

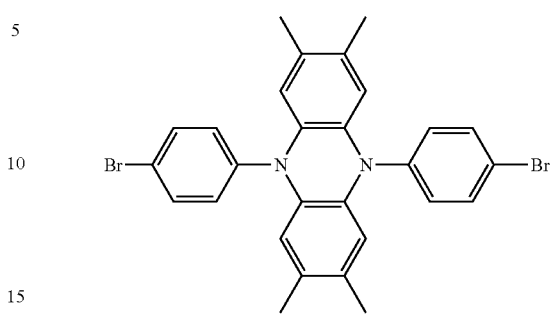

(2.73 g, 5 mmol), diphenylamine

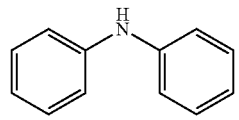 [SMILES: c1ccc(Nc2ccccc2)cc1]

(2.03 g, 12 mmol), palladium (II) acetate (0.18 g, 0.8 mmol), and tri-tert-butylphosphine tetrafluoroborate (0.68 g, 2.4 mmol) are added into a dual mouth bottle of 250 mL, and then NaOt-Bu (1.16 g, 12 mmol) is added into a glovebox, toluene of 100 mL free of water and oxygen is added into the reaction solution in advance under an atmosphere of argon gas for reaction at 120° C. by 24 hours. The reaction solution above are cooled to a room temperature, and the reaction solution is poured into ice water of 200 mL, extracts of organic phase are extracted three times by dichloromethane to combine the extract of organic phase, and the extracts of organic phase combined are spun to form silicone. Separation and purification of column chromatography (dichloromethane:hexane, v:v, 1:5) is implemented to acquire white powder of 2.9 g, and a yield rate is 80%. After spectrometric analysis, MS (EI)m/z: [M]+ is 720.31.

Third Embodiment

A hole transport material 3 is compounded, a compounding path there of is as follows:

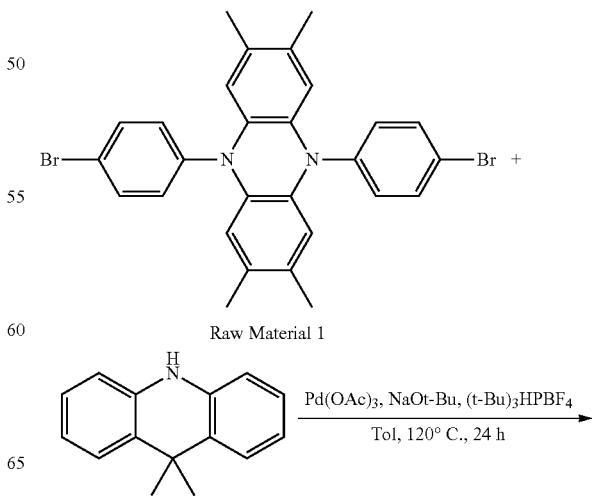
Raw Material 1

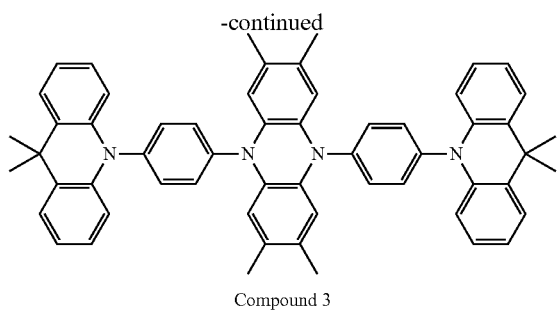

Compound 3

A raw material 1

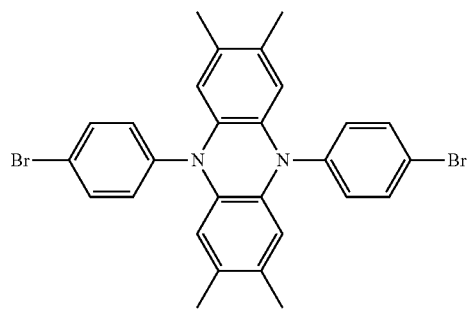

(2.73 g, 5 mmol), N,N-dimethylacridine (2.50 g, 12 mmol), palladium (II) acetate (0.18 g, 0.8 mmol) 和 tri-tert-butylphosphine tetrafluoroborate (0.68 g, 2.4 mmol) are added into a dual mouth bottle of 250 mL, and then NaOt-Bu (1.16 g, 12 mmol) is added into a glovebox, toluene of 100 mL free of water and oxygen is added into the reaction solution in advance under an atmosphere of argon gas for reaction at 120° C. by 24 hours. The reaction solution above are cooled to a room temperature, and the reaction solution is poured into ice water of 200 mL, extracts of organic phase are extracted three times by dichloromethane to combine the extract of organic phase, and the extracts of organic phase combined are spun to form silicone. Separation and purification of column chromatography (dichloromethane: hexane, v:v, 1:5) is implemented to acquire white powder of 3.8 g, and a yield rate is 95%. After spectrometric analysis, MS (EI)m/z: [M]+ is 804.31.

An electrochemical energy level of the target molecule is as the following Chart 1.

|  | HOMO (eV) | LUMO (eV) |
| --- | --- | --- |
| compound 1 | −5.53 | −2.53 |
| compound 2 | −5.61 | −2.53 |
| compound 3 | −5.58 | −2.54 |

Performance data of the device is as follows:

| Device | Hole transport layer | Highest current efficiency (cd/A) | (CIEx, CIEy) | Maximum external quantum efficiency (%) |
| --- | --- | --- | --- | --- |
| Device 1 | Compound 1 | 40.3 | (0.685, 0.291) | 38.3% |
| Device 2 | Compound 2 | 41.7 | (0.685, 0.292) | 39.6% |
| Device 3 | Compound 3 | 40.8 | (0.685, 0.291) | 38.7% |

By inspecting various physical and chemical indexes of different compounded compounds, a hole transport material with high efficiency is presented, an OLED electroluminescent device with a long lifespan is acquired, which is a display device based on electroluminescent device.

With reference to FIG. 1, the present invention also provides an electroluminescent device comprising a glass and total reflection (ITO/Ag/ITO) underlay layer 1, a hole injection layer 2: a P-dopant and transport layer 3 (hole transport layer), electron blocking layer 4, light emitting layer 5, hole blocking layer 6, an electron transport layer 7, an electron injection layer 8, translucent electrode 9, and an optical coupling output layer 10 that are sequentially stacked on one another.

The substrate layer 1 comprises glass and a total reflection underlay layer including an indium tin oxide (ITO) layer, an Ag layer and an ITO layer that are stacked sequentially. The Ag layer is a reflective surface configured to make an output light emitted from a top of the device.

The hole injection layer 2 is configured to transport holes the ITO layers into an organic light emitting diode (OLED) device, and is made of MoO3.

The hole transport layer 3 is configured to transport the holes injected and is capable of adjusting a resonant wavelength of a microcavity by adjusting a thickness of the hole transport layer, and the hole transport layer is made of the hole transport material.

The electron blocking layer 4 is configured to block and hold electrons injected into the light emitting layer in the light emitting layer to prevent the electrons from being transported to the hole transport layer, and to restrict a composite region of excitons in the light emitting layer, and the electron blocking layer is made of (4-[1-[4-[bis(4-methylphenyl)amino]phenyl]cyclohexyl]-N-(3-methylphenyl)-N-(4-methylphenyl)aniline (TAPC).

The light emitting layer 5 is configured to combine the holes and the electrons to form excitons, a fluorescent material emits light by the excitons, and the light emitting layer is made of 4,4'-bis(9-carbazole)biphenyl: tris(2-phenylpyridine)iridium (III) doped.

The hole blocking layer 6 is configured to block and hold holes injected into the light emitting layer in light emitting layer to prevent the holes from being transported to the electron transport layer, and to restrict, and to restrict a composite region of excitons in the light emitting layer, and the hole blocking layer is made of 1,3,5-Tris(3-pyridyl-3-phenyl)benzene (Tm3PyPB).

The electron transport layer 7 is configured to transport the electrons injected, is made of 1,3,5-Tris(3-pyridyl-3-phenyl)benzene Tm3PyPB and 8-Hydroxyquinoline aluminum salt (LiQ), and the electron transport layer is configured to transport the electrons to the light emitting layer.

The electron injection layer 8 is configured to inject electrons into the OLED device, and is generally made of Yb or LiF.

The translucent cathode layer 9 is configured to translucent emission and transmission, is capable of adjusting strength of the microcavity, and is made of magnesium/silver translucent electrode;

The coupling output layer 10 is configured to implement coupling extraction to light and enhance light output rate, and the coupling output layer is made of 4,4',4''-tris[4-(carbazol-9-yl)phenyl]amine (TCTA).

The structure of the above electroluminescent device for functions of the microcavity and requirement of enhanced color gamut of light of the device for applications, the hole transport material is disposed on the third layer and improves the efficiency of the device by increasing mobility.

The above is only preferred embodiments of the present invention. It should be noted that a person of ordinary skill in the art can make several improvements and modifications without departing from the principle of the present invention. These improvements and modifications should also be considered to be within the scope of protection of the present invention.

INDUSTRIAL APPLICABILITY

The subject matter of the present invention can be manufactured and used in industries and therefore has industrial applicability.

What is claimed is:
1. An electroluminescent device, comprising:
a substrate layer, a hole injection layer, a transport layer, an electron blocking layer, a light emitting layer, a hole blocking layer, an electron transport layer, an electron injection layer, a translucent electrode, and an optical coupling output layer that are sequentially stacked on one another;
wherein the substrate layer comprises glass and a total reflection underlay layer including an indium tin oxide (ITO) layer, an Ag layer and an ITO layer that are stacked sequentially, and the Ag layer is a reflective surface configured to make an output light emitted from a top of the device;
wherein the hole injection layer is configured to inject holes from the ITO layers into an organic light emitting diode (OLED) device, and is made of MoO3;
wherein the hole transport layer is configured to transport the holes injected and is capable of adjusting a resonant wavelength of a microcavity by adjusting a thickness of the hole transport layer, and the hole transport layer is made of a hole transport material comprising a central core made of tetramethyldihydrophenazine, wherein a structural formula of the hole transport material is:

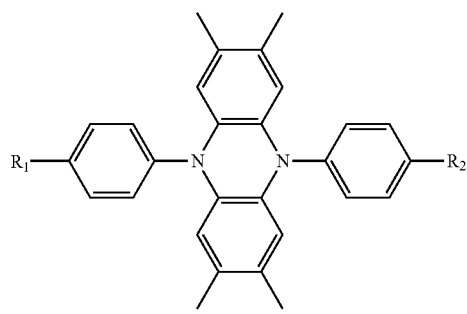 [SMILES: Cc1cc2c(cc1C)N(c1ccc(Br)cc1)c1cc(C)c(C)cc1N2c1ccc(Br)cc1]

wherein each of the R1 group and the R2 group is selected from structural formulas as follows:

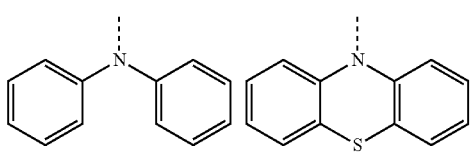

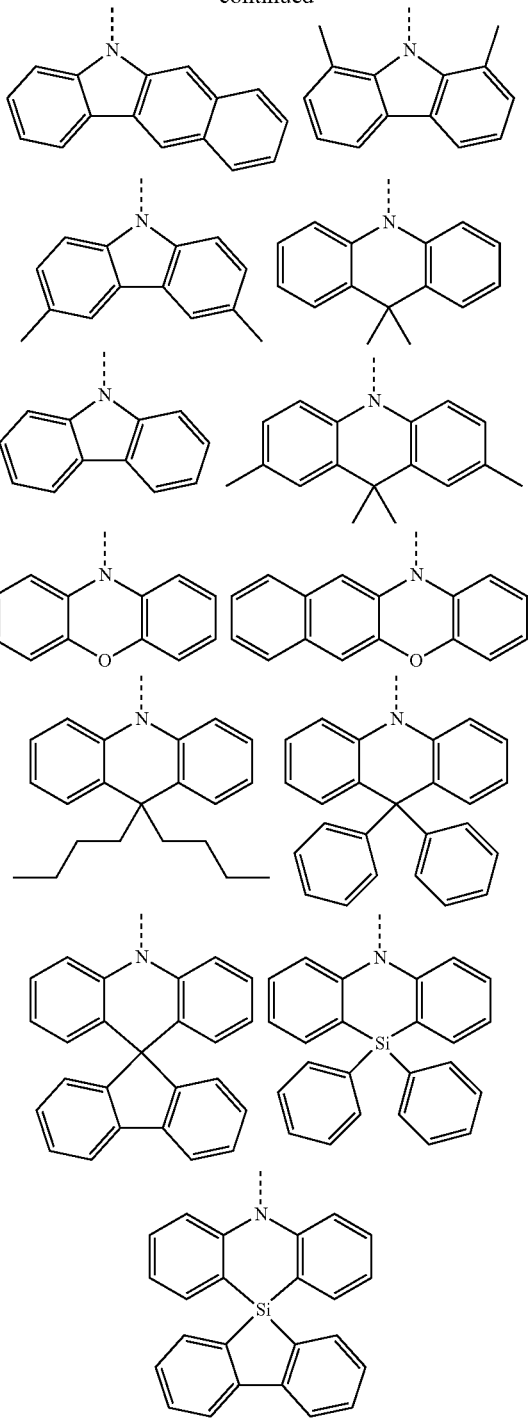

wherein the electron blocking layer is configured to block and hold electrons injected into the light emitting layer in the light emitting layer to prevent the electrons from being transported to the hole transport layer, and to restrict a composite region of excitons in the light emitting layer, and the electron blocking layer is made of (4-[1-[4-[bis(4-methylphenyl)amino]phenyl]cyclohexyl]-N-(3-methylphenyl)-N-(4-methylphenyl)aniline (TAPC);
wherein the light emitting layer is configured to combine the holes and the electrons to form excitons, a fluorescent material emits light by the excitons, and the light emitting layer is made of 4,4'-bis(9-carbazole)biphenyl: tris(2-phenylpyridine)iridium (Ill) doped;

wherein the hole blocking layer is configured to block and hold holes injected into the light emitting layer in light emitting layer to prevent the holes from being transported to the electron transport layer, and to restrict, and to restrict a composite region of excitons in the light emitting layer, and the hole blocking layer is made of 1,3,5-Tris (3-pyridyl-3-phenyl)benzene (Tm3PyPB);

wherein the electron transport layer is configured to transport the electrons injected, is made of 1,3,5-Tris (3-pyridyl-3-phenyl)benzene Tm3PyPB and 8-Hydroxyquinoline aluminum salt (LiQ), and the electron transport layer is configured to transport the electrons to the light emitting layer;

wherein the electron injection layer is configured to inject electrons into the OLED device;

wherein the translucent electrode is configured to translucent emission and transmission, is capable of adjusting strength of the microcavity, and is made of magnesium/silver translucent electrode; and wherein the coupling output layer is configured to implement coupling extraction to light and enhance light output rate, and the coupling output layer is made of 4,4',4"-tris[4-(carbazol-9-yl)phenyl]amine (TCTA).

\* \* \* \* \*